United States Patent
Bang et al.

(10) Patent No.: US 12,257,041 B2
(45) Date of Patent: Mar. 25, 2025

(54) METHOD, DEVICE, AND COMPUTER PROGRAM FOR PREDICTING BRAIN TISSUE LESION DISTRIBUTION

(71) Applicant: Samsung Life Public Welfare Foundation, Seoul (KR)

(72) Inventors: Oh Young Bang, Seoul (KR); Yoon-Chul Kim, Seoul (KR); Jong-Won Chung, Seoul (KR); Woo-Keun Seo, Seoul (KR); Gyeong-Moon Kim, Seoul (KR); Geon Ha Kim, Gwacheon si (KR); Pyoung Jeon, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 595 days.

(21) Appl. No.: 17/099,008

(22) Filed: Nov. 16, 2020

(65) Prior Publication Data
US 2021/0393212 A1 Dec. 23, 2021

(30) Foreign Application Priority Data
Jun. 22, 2020 (KR) .......................... 10-2020-0075985

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0042* (2013.01); *A61B 5/7267* (2013.01);
(Continued)

(58) Field of Classification Search
CPC . G06T 2207/30016; G06T 2207/10088; G06T 7/0012; A61B 5/055; A61B 6/507;
(Continued)

(56) References Cited

U.S. PATENT DOCUMENTS
2020/0357120 A1   11/2020   Kang et al.

FOREIGN PATENT DOCUMENTS
KR          10-2001398 B1     7/2019
KR       10-2020-0055690 A    5/2020

OTHER PUBLICATIONS

McKinley, Richard, et al. "Fully automated stroke tissue estimation using random forest classifiers (FASTER)." Journal of Cerebral Blood Flow & Metabolism 37.8 (2017): 2728-2741. (Year: 2017).*
(Continued)

*Primary Examiner* — Raphael Schwartz
(74) *Attorney, Agent, or Firm* — McCarter & English, LLP

(57) ABSTRACT

According to an embodiment of the present disclosure, there is provided a method of predicting a brain tissue lesion distribution, the method including: a model learning operation of learning a prediction model for predicting a brain tissue lesion distribution of a subject by using brain image data of a plurality of previous patients; an input obtaining operation of obtaining input data from brain image data of the subject; and an output operation of generating output image data including information on the lesion distribution after recanalization treatment for the subject, by using the prediction model. The prediction model includes a success prediction model that is learned by using data of patients in which recanalization treatment is successful among the plurality of previous patients, and a failure prediction model that is learned by using data of patients in which recanalization treatment fails among the plurality of previous patients.

9 Claims, 11 Drawing Sheets

(51) Int. Cl.
  *A61B 6/50* (2024.01)
  *G06F 18/214* (2023.01)
  *G06F 18/22* (2023.01)
  *G06T 7/00* (2017.01)
  *G06V 10/25* (2022.01)
  *G06V 10/50* (2022.01)
  *G06V 10/75* (2022.01)
  *G06V 10/80* (2022.01)
  *G06V 10/82* (2022.01)
  *G16H 30/40* (2018.01)
  *G16H 50/20* (2018.01)
  *G16H 50/50* (2018.01)

(52) U.S. Cl.
  CPC .......... *A61B 5/7275* (2013.01); *G06F 18/214* (2023.01); *G06F 18/22* (2023.01); *G06T 7/0014* (2013.01); *G16H 30/40* (2018.01); *G16H 50/20* (2018.01); *G16H 50/50* (2018.01); *A61B 6/501* (2013.01); *A61B 2576/026* (2013.01); *G06T 2207/20076* (2013.01); *G06T 2207/20081* (2013.01); *G06T 2207/30016* (2013.01); *G06T 2207/30096* (2013.01); *G06V 10/25* (2022.01); *G06V 10/50* (2022.01); *G06V 10/758* (2022.01); *G06V 10/811* (2022.01); *G06V 10/82* (2022.01); *G06V 2201/031* (2022.01)

(58) Field of Classification Search
  CPC .. A61B 6/504; A61B 5/0042; A61B 2576/026
  See application file for complete search history.

(56) References Cited

OTHER PUBLICATIONS

Baliyan, Vinit, et al. "Diffusion weighted imaging: technique and applications." World journal of radiology 8.9 (2016): 785. (Year: 2016).*

Radiopaedia, Modified treatment in cerebral ischemia (mTICI) score, https://radiopaedia.org/articles/modified-treatment-in-cerebral-ischaemia-mtici-score?lang=us, May 1, 2018 (Year: 2018).*

Kemmling, André, et al. "Multivariate dynamic prediction of ischemic infarction and tissue salvage as a function of time and degree of recanalization." Journal of Cerebral Blood Flow & Metabolism 35.9 (2015): 1397-1405. (Year: 2015).*

Kim, Yoon-Chul et al.: "Novel estimation of penumbra zone based on infarct growth using machine learning techniques in acute ischemic stroke", The 9th Japan-Korea Joint Stroke Conference Nov. 16, 2019, p. 184.

* cited by examiner (a)

(b)

METHOD, DEVICE, AND COMPUTER PROGRAM FOR PREDICTING BRAIN TISSUE LESION DISTRIBUTION

CROSS-REFERENCE TO RELATED APPLICATION

This application is based on and claims priority under 35 U.S.C. § 119 to Korean Patent Application No. 10-2020-0075985, filed on Jun. 22, 2020, in the Korean Intellectual Property Office, the disclosure of which is incorporated by reference herein in its entirety.

BACKGROUND

1. Field

The present disclosure relates to a method, a device, and a computer program for predicting a brain tissue lesion distribution in a patient with cerebral infarction.

2. Description of Related Art

Cerebral ischemia is a condition, in which a blood vessel in the brain is occluded and tissue cells affected by the occlusion are deprived of oxygen. For example, the cerebral artery is occluded when either (1) blood clot is formed due to atrial fibrillation and is moved up to the cerebral artery to block the blood stream or (2) atherosclerotic plaques are built up in the endothelium of the cerebral artery and are suddenly ruptured to block the blood stream. As the cerebrovascular blood vessels are occluded and the supply of blood to the brain tissues is critically limited, the affected area undergoes hypoperfusion and, if untreated, would become infarcted over time, causing neurological symptoms such as impaired consciousness or physical paralysis.

In the case where cerebral ischemia occurs, treatment is performed in which the blocked blood vessels are recanalized early to restore blood flow to the brain before the brain tissues are completely infarcted. Neuroimaging studies in acute ischemic stroke demonstrate that infarcted (i.e., ischemic core) and hypoperfused lesions can be estimated by using diffusion weighted image (DWI) and perfusion weighted image (PWI), respectively, and the extent of penumbra (i.e., the site of hypoperfusion without ischemic core) is a good indicator of treatment effect and favorable clinical outcome in early reperfusion.

However, the estimation of the penumbra zone by relying on pre-treatment DWI and PWI data may have limitations, since infarct progression may be different in individual patients. It would be advantageous to develop an improved method that is data-driven based on machine learning concept, where previous individual cases of pre-treatment and post-treatment image data are utilized for learning, and visualizes maps/distributions of voxel-wise tissue fate, prior to treatment decision, using machine learning models in cases of successful and unsuccessful recanalization.

SUMMARY

The present disclosure is given to provide a prediction device of a prognosis, a method therefor, and a computer program, in which for a patient with cerebral infarction, by predicting and imaging a degree of brain tissue damage at a time of success or failure of recanalization treatment by using a machine learning model, it is possible to compare and predict distributions of final brain tissue damage and select a treatment policy based thereon.

Additional aspects will be set forth in part in the description which follows and, in part, will be apparent from the description, or may be learned by practice of the presented embodiments of the disclosure.

According to an embodiment of the present disclosure, there is provided a method of predicting a brain tissue lesion distribution including a model learning operation of learning a prediction model for predicting a brain tissue lesion distribution in a subject by using brain image data of a plurality of previous patients; an input obtaining operation of obtaining input data from brain image data of the subject; an input operation of inputting the input data into the prediction model; and An output operation of generating output image data including information on the lesion distribution after recanalization treatment for the subject, by using the prediction model, wherein the prediction model includes a 'success' prediction model that is learned by using brain image data of patients who underwent successful recanalization treatment among the plurality of previous patients, and a 'failure' prediction model that is learned by using brain image data of patients in which recanalization treatment failed among the plurality of previous patients.

The model learning operation may include an image matching operation of matching different types of the brain image data of each of the plurality of previous patients; an operation of calculating deformation data from the brain image data and selecting a region of interest corresponding to the lesion site; an operation of labeling the region of interest with a preset value according to whether or not each voxel corresponds to a lesion; and a learning input obtaining operation of obtaining learning input data by extracting the deformation data for each voxel with respect to the region of interest.

The brain image data matched in the image matching operation may include first diffusion weighted image (DWI) data obtained before treatment, perfusion weighted image (PWI) data before treatment, and second diffusion weighted image (DWI) data obtained after treatment.

The calculation/selection operation may include an operation of calculating an apparent diffusion coefficient (ADC) from the first diffusion weighted image (DWI) data; an operation of calculating relative time to peak (rTTP) from the perfusion weighted image (PWI) data before treatment; and an operation of selecting the region of interest from the first diffusion weighted image (DWI) data, the perfusion weighted image (PWI) data before treatment, and the second diffusion weighted image (DWI) data. The selection process is automatically performed by an algorithm.

The model learning operation may further include an operation of selecting a symmetric region corresponding to a normal site from the brain image data; and an operation of extracting the deformation data for each voxel with respect to the symmetric region to obtain the learning input data. The symmetric region may be selected for the first diffusion weighted image (DWI) data and the perfusion weighted image (PWI) data before treatment.

The output operation may include a first output operation of inputting the input data into the failure prediction model to generate first output image data including information on the lesion distribution after failure of the recanalization treatment for the subject; and a second output operation of inputting the input data into the success prediction model to generate second output image data including information on the lesion distribution after success of the recanalization treatment for the subject.

The output operation may further include an operation of comparing the first output image data and the second output image data to determine whether or not the recanalization treatment is to be performed.

According to an embodiment of the present disclosure, a device for predicting a brain tissue lesion distribution after treatment of a subject, includes a control unit and an output unit, and the control unit learns a prediction model for predicting a brain tissue lesion distribution of the subject by using brain image data of a plurality of previous patients, obtains input data from brain image data of the subject, and inputs the input data into the prediction model. The output unit generates output image data including information on the lesion distribution after recanalization treatment for the subject by using the prediction model. The prediction model includes a success prediction model that is learned by using brain image data of patients in which recanalization treatment is successful among the plurality of previous patients, and a failure prediction model that is learned by using brain image data of patients in which recanalization treatment fails among the plurality of previous patients.

The control unit may match different types of brain image data of each of the plurality of previous patients, calculate deformation data from the brain image data and select a region of interest corresponding to a lesion site, label the region of interest with a preset value according to whether or not each voxel corresponds to a lesion, and obtain learning input data by extracting the deformation data for each voxel with respect to the region of interest.

The matched brain image data may include first diffusion weighted image (DWI) data obtained before treatment, perfusion weighted image (PWI) data before treatment, and second diffusion weighted image (DWI) data obtained after treatment.

The control unit may calculate an apparent diffusion coefficient (ADC) from the first diffusion weighted image (DWI) data, calculate relative time to peak (rTTP) from the perfusion weighted image (PWI) data before treatment to obtain an rTTP map, and select the region of interest from the first diffusion weighted image (DWI) data, the perfusion weighted image (PWI) data before treatment, and the second diffusion weighted image (DWI) data.

The control unit may select a symmetric region corresponding to a normal site from the brain image data and extract the deformation data for each voxel with respect to the symmetric region to obtain the learning input data. The symmetric region may be selected for the first diffusion weighted image (DWI) data and the perfusion weighted image (PWI) data before treatment.

The output unit may generate first output image data including information on the lesion distribution after failure of recanalization treatment for the subject based on the input data input into the failure prediction model, and generate second output image data including information on the lesion distribution after success of the recanalization treatment for the subject based on the input data input into the success prediction model.

The output unit may determine whether or not the recanalization treatment is to be performed for the subject by comparing the first output image data with the second output image data.

The method of predicting the lesion distribution of the present disclosure described above may be stored in a medium as a computer program to be executed by using a computer.

BRIEF DESCRIPTION OF THE DRAWINGS

The above and other aspects, features, and merits of certain embodiments of the disclosure will be more apparent from the following description taken in conjunction with the accompanying drawings, in which.

DETAILED DESCRIPTION

Figure 1:
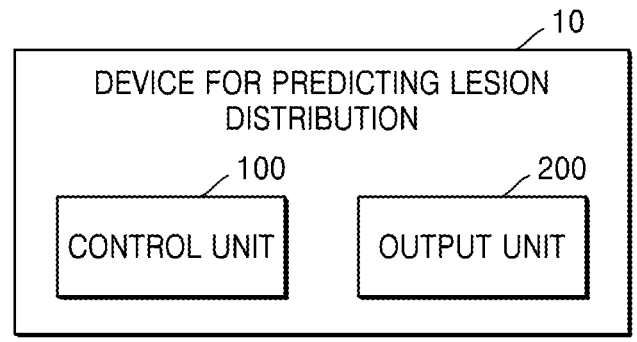
FIG. 1 is a block diagram schematically illustrating a configuration of a device of predicting a brain tissue lesion distribution according to an embodiment of the present disclosure.

Reference will now be made in detail to examples, examples of which are illustrated in the accompanying drawings, wherein like reference numerals refer to like elements throughout. In this regard, the present examples may have different forms and should not be construed as being limited to the descriptions set forth herein. Accordingly, the examples are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Since the present disclosure may apply various transformations and have various embodiments, certain embodiments will be illustrated in the drawings and described in detail in the detailed description. Effects and characteristics of the present disclosure, and a method of achieving them will be apparent with reference to the embodiments described below in detail together with the drawings. However, the present disclosure is not limited to the embodiments disclosed below and may be implemented in various forms.

Some embodiments of the present disclosure may be represented by functional block configurations and various processing operations. Some or all of these functional blocks may be implemented by various numbers of hardware and/or software configurations that perform certain functions. For example, the functional blocks of the present disclosure may be implemented by one or more microprocessors or may be implemented by circuit configurations for a prescribed function. In addition, for example, the functional blocks of the present disclosure may be implemented in various programming or scripting languages. The functional blocks may be implemented by an algorithm executed on one or more processors. In addition, the present disclosure may employ techniques of the related art for electronic environment setting, signal processing, and/or data processing. Terms such as "mechanism", "element", "means" and "configuration" may be widely used and are not limited to mechanical and physical configurations.

In addition, connecting lines or connecting members between configuration elements illustrated in the drawings are merely illustrative of functional connections and/or physical or circuit connections. In an actual device, connections between the configuration elements may be represented by various functional connections, physical connections, or circuit connections that may be replaced or added.

In the following embodiments, terms such as first and second are not used in a limiting meaning but are used for the purpose of distinguishing one configuration element from another configuration element. In the following embodiments, a singular expression includes a plural expression unless a context clearly indicates otherwise. In the following embodiments, terms such as include or have refer that the characteristics or configuration elements described in the specification are present, and do not preclude a possibility of adding one or more other characteristics or configuration elements in advance.

In a case where a certain embodiment may be implemented differently, certain operations may be performed differently from the described order. For example, two operations described in succession may be performed substantially simultaneously or may be performed in an order opposite to the described order.

In the present specification, the term "brain image" refers to an image that visualizes an internal structure and/or a function of the brain through a direct or indirect method, and may include a magnetic resonance image, a computed tomography (CT) image, a positron emission tomography (PET) image, a single photon emission computed tomography (SPECT) image, and the like. In the present specification, the term "magnetic resonance imaging (MRI)" refers to a diagnostic technology that uses a magnetic field to generate an image or photograph of an internal structure, and an image obtained through it.

In the present specification, the term "diffusion weighted image (DWI)" refers to image data obtained through a technique of measuring an irregular movement of water protons in tissue, that is, a rate of diffusion, and in general, is an image processing method capable of measuring cerebral infarction or lesion caused by cerebrovascular occlusion. Through the detection of such signal changes, various ischemic brain tissue damage indicators such as a brain tissue damage site and a damage volume may be measured. In this case, the diffusion rate is determined by a b-value representing an intensity of a gradient magnetic field.

In the present specification, the term "perfusion weighted image (PWI)" refers to an image obtained by a technique of continuously obtaining multiple frames of a brain image for 1 to 2 minutes with a time resolution of 1 to 2 seconds during a first pass of a bolus of contrast agent. For the perfusion weighted image, the dynamic susceptibility contrast (DSC) technique uses long echo time in pulse sequence to enhance T2 or T2* relaxation effect and is commonly employed in acute stroke imaging. In DSC, the contrast agent affects reduced MRI signals by inducing a large degree of magnetic susceptibility. In a case of brain tissue with ischemia due to blockage of cerebrovascular blood vessels, the DSC image shows darker signals in normal brain tissue than in ischemic tissue at the time of first pass because the contrast agent is not well supplied to the ischemic tissue. In addition, a time point, at which a DSC MRI signal becomes a minimum, is delayed in the ischemic tissue, compared to normal brain tissue.

In the present specification, the term "voxel" refers to a regular grid unit in a 3D space and may refer to a pixel in an image of a 2D plane.

Hereinafter, embodiments of the present disclosure will be described in detail with reference to the accompanying drawings, and when describing with reference to the drawings, the same or corresponding configuration elements are assigned with the same reference numerals, and redundant descriptions thereof will be omitted.

Figure 2:
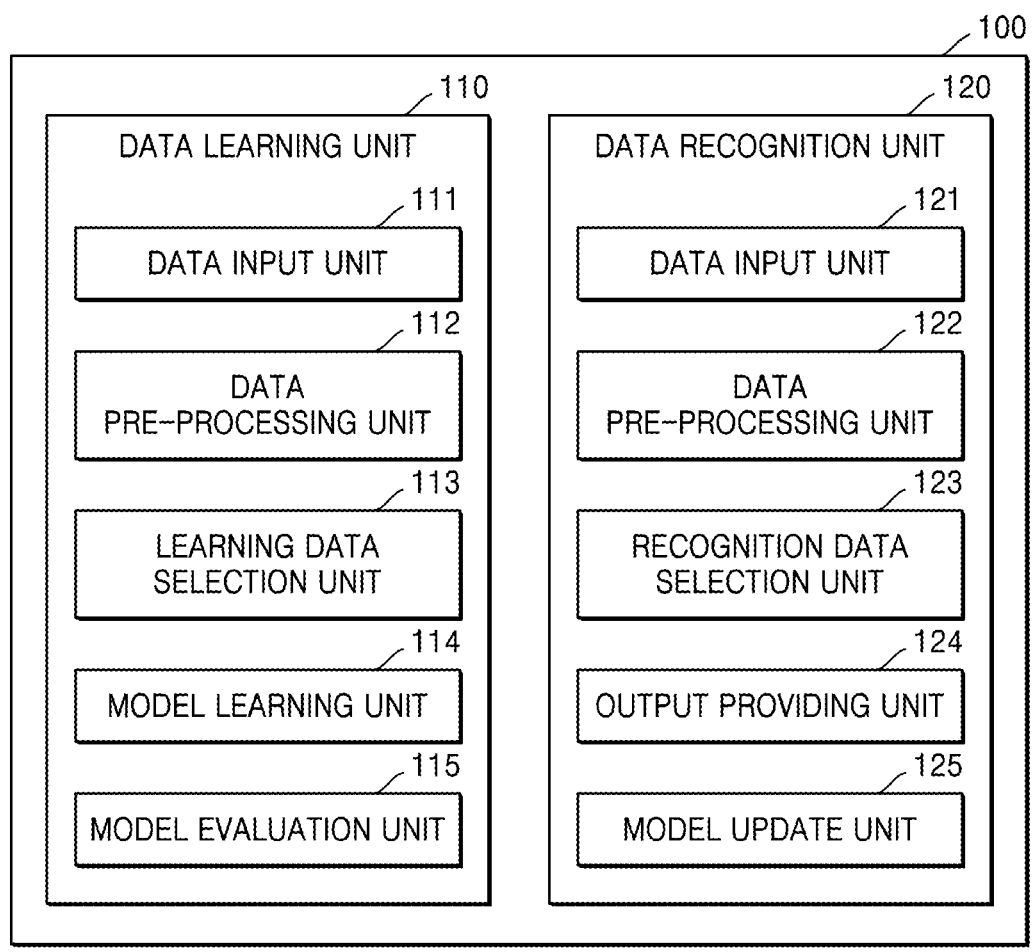
FIG. 2 is a block diagram illustrating a configuration of a control unit according to an embodiment of the present disclosure.

FIG. 1 is a block diagram schematically illustrating a configuration of a prediction device 10 of a lesion distribution according to an embodiment of the present disclosure, and FIG. 2 is a block diagram illustrating a configuration of a control unit according to an embodiment of the present disclosure.

The distribution of the prediction device 10 of the lesion distribution of the present disclosure (hereinafter may be referred to as a "prediction device 10") is a device that receives brain image data before treatment of the subject, processes the data, and predicts and outputs the distribution of the brain tissue lesion of the subject. In this case, the prediction device 10 may perform the above-described output operation by using the prediction model.

The prediction device 10 may include a control unit 100 and an output unit 200. The prediction device 10 may further include general-purpose configuration elements other than the configuration elements illustrated in FIG. 1.

The control unit 100 may include all types of devices capable of processing data, such as a processor. The control unit 100 may perform an operation of overall controlling the prediction device 10 by using a processor. Here, the 'processor' may refer, for example, a data processing device embedded in hardware, which has a circuit physically structured to perform a function represented by a code or command included in a program. As described above, as an example of the data processing device built into hardware, a processing device such as a microprocessor, a central processing unit (CPU), a processor core, a multiprocessor, an application-specific integrated circuit (ASIC), or a field programmable gate array (FPGA) may be included, but the scope of the present disclosure is not limited thereto.

Referring to FIG. 2, the control unit 100 may include a data learning unit 110 and a data recognition unit 120.

The data learning unit 110 may learn a criterion for predicting the distribution of the brain tissue lesion of a subject by using brain image data of a plurality of previous patients. The prediction model of the present disclosure may be learned through the data learning unit 110. The term previous patients may refer to data providers who provide learning input data to the prediction model as patients with cerebral infarction and stroke. The subject may be, like the previous patients, a patient with cerebral infarction due to cardioembolic clot by arteriosclerosis in cerebrovascular, and occlusion of cerebral blood vessels by the embolism derived from the heart, but the subject is not necessarily limited thereto. The subject may refer to a test patient who is provided with information on prediction about the brain tissue lesion distribution through the prediction device 10 of the lesion distribution or a method therefor of the present disclosure.

The prediction model of the present disclosure includes a success prediction model (successful recanalization (SR)) that is learned by using brain image data of patients in which recanalization treatment is successful among a plurality of previous patients, and a failure prediction model (unsuccessful recanalization (UR)) that is learned by using brain image data of patients in which recanalization treatment fails among the plurality of previous patients. A method of predicting the lesion distribution by using the two prediction models (SR and UR) will be described in more detail in FIG. 5 to be described below.

The prediction model may be generated by various types of machine learning techniques. The prediction model may be a model based on an artificial neural network, and a network structure of the artificial neural network does not limit the present disclosure.

The data learning unit 110 may include a data input unit 111, a data pre-processing unit 112, a learning data selection unit 113, a model learning unit 114, and a model evaluation unit 115.

The data input unit 111 may receive brain image data, for example, magnetic resonance imaging (MRI) data, from an external brain imaging device or a medical database (DB) that is previously stored. In the present disclosure, the brain image data may include the diffusion weighted image (DWI) and the perfusion weighted image (PWI).

The data pre-processing unit 112 may pre-process the input data so that the data input for learning/training to predict the lesion distribution of the subject may be used. The data pre-processing unit 112 may process the input data into a preset format so that the model learning unit 114 to be described below may use the input data for learning to predict the lesion distribution. The data pre-processing unit 112 may perform an operation of selecting/generating learning input data from the input brain image.

More particularly, the data pre-processing unit 112 (hereinafter may be referred to as the "pre-processing unit 112") may perform operations to be described below.

The pre-processing unit 112 may co-register different types of the brain image data of each of the plurality of previous patients. The brain image data may include magnetic resonance imaging (MRI) data. The MRI data may include diffusion weighted imaging (DWI) data, perfusion weighted imaging (PWI) data, fluid attenuated inversion recovery (FLAIR) image data, susceptibility weighted imaging (SWI) data, T1 weighted image data, and T2 weighted image data, but the type of MRI data is not limited thereto.

The matched brain image data in the present disclosure may include a first diffusion weighted image (DWI) obtained before treatment, a perfusion weighted image (PWI) before treatment, and a second diffusion weighted image (DWI) obtained after treatment.

The prediction device 10 may receive magnetic resonance imaging data from an external magnetic resonance imaging device or a medical database (DB) that is previously stored, but the present disclosure is not limited thereto.

The pre-processing unit 112 may calculate parameter maps from the brain image data. The parameter maps may include an apparent diffusion coefficient (ADC) obtained by processing the DWI data, time to peak (TTP) obtained by processing the PWI data, and relative time to peak (rTTP), but are not limited thereto. The calculation process of rTTP map is illustrated in detail in FIG. 6.

Particularly, the pre-processing unit 112 may calculate the ADC from the first diffusion weighted image (DWI) data and calculate the rTTP from the perfusion weighted image (PWI) data before treatment. The pre-processing unit 112 may select a region of interest from the second diffusion weighted image (DWI) data. The region of interest LS (see FIG. 7) may be a region corresponding to the brain lesion of the data provider or the subject.

The pre-processing unit 112 may select the region of interest LS (see FIG. 7) corresponding to the brain lesion site of the data provider or the subject, and a symmetric area C_LS (see FIG. 7) corresponding to the normal site. In this case, the region of interest LS may include a first central voxel and a first peripheral voxel around the first central voxel, and the symmetric region C_LS may include a second central voxel and a second peripheral voxel around the second central voxel.

It may be determined whether or not each of voxels divided in the region of interest LS and the symmetric region C_LS finally corresponds to a lesion. That is, there may be a voxel that is determined to be no lesion even within the region of interest (LS), or a voxel that is determined to be the lesion also within the symmetric region C_LS.

The pre-processing unit 112 may label the region of interest with a preset value according to whether or not each voxel v corresponds to a lesion. The pre-processing unit 112 may obtain the learning input data by extracting the above-described deformation data for each voxel for the region of interest and the symmetric region. Operations of the pre-processing unit 112 will be described in more detail in FIG. 7 to be described below.

The learning data selection unit 113 may select data necessary for learning from among pre-processed learning input data. The selected data may be provided to the model learning unit 114. The learning data selection unit 113 may select data necessary for learning from among the pre-processed data according to a preset criterion. The learning data selection unit 113 may select data according to a preset criterion by learning by the model learning unit 114 to be described below.

The model learning unit 114 may learn a criterion for predicting the lesion distribution of the subject based on the learning data, with a configuration element capable of corresponding to the above-described "prediction model". In particular, since the prediction model in the present disclosure includes the success prediction model and the failure prediction model, the model learning unit 114 may learn the criterion for each of the success/failure prediction models. In addition, the model learning unit 114 may learn which learning data to use to predict the lesion distribution, that is, learn a criterion for selecting the learning input data.

In addition, the model learning unit 114 may learn a data recognition model used to predict the lesion distribution by using the learning data. In this case, the data recognition model may be a pre-built model. When the data recognition model is learned, the model learning unit 114 may store the learned data recognition model in a memory of an electronic device including the data recognition unit 120. Alternatively, the model learning unit 114 may store the learned data recognition model in a memory of a server connected to the electronic device through a wired or wireless network.

The model evaluation unit 115 may input evaluation data into the data recognition model, and in a case where a recognition outcome output from the evaluation data does not satisfy a prescribed criterion, allow the model learning unit 114 to learn again. In this case, the evaluation data may be preset data for evaluating the data recognition model.

The data recognition unit 120 may predict the brain tissue lesion distribution of the subject based on the input data of the subject. The data recognition unit 120 may predict the lesion distribution after treatment from brain image data including information on the lesion distribution before treatment of the subject by using the learned prediction model. The data recognition unit 120 may obtain the input data according to a preset criterion by learning and input the input data into the prediction model to predict the lesion distribution. The 'preset criterion' may be an algorithm for processing data performed by the data learning unit 110 on the brain image data of the plurality of previous patients. In other words, the data selection, generation, or pre-processing operations for the brain image data of the plurality of previous patients used for the learning of the prediction model may be applied in the same manner or similarly for the brain image data of the subject for which the lesion distribution is to be predicted. In addition, an outcome value output by the data recognition model by using data obtained through the data recognition unit 120 as an input value may be used to update the data recognition model.

The data recognition unit 120 may include a data input unit 121, a data pre-processing unit 122, a recognition data selection unit 123, an output providing unit 124, and a model update unit 125.

The data input unit 121 may input the brain image data before treatment of the subject as data necessary for predicting the lesion distribution. The pre-processing unit 122 may pre-process the received data so that the input data may be used. The pre-processing unit 122 may process the input data into a preset format so that the output providing unit 124 to be described below may use the input data to predict the lesion distribution.

The pre-processing unit 122 may pre-process the brain image data of the subject by using the same algorithm as that of the pre-processing unit 112 of the data learning unit 110 described above. The pre-processing unit 122 may perform operations to be described below with respect to the brain image data of the subject, and detailed contents may refer to the description of the pre-processing unit 112 of the data learning unit 110 described above.

The pre-processing unit 122 may match different types of the brain image data of the subject, and the brain image data may include the first DWI data, the PWI data before treatment, and the second DWI data that is data after treatment (for example, after 7 days of the treatment). The pre-processing unit 122 may calculate the deformation data from the brain image data and select the region of interest corresponding to the lesion region. The pre-processing unit 122 may label the region of interest with a preset value according to whether or not each voxel corresponds to the lesion, and obtain the learning input data by extracting the deformation data for each voxel for the region of interest and the symmetric region.

Operations of the above-described pre-processing unit 122 will be described in more detail with reference to FIGS. 6 to 8 to be described below.

The recognition data selection unit 123 may select data necessary for predicting the lesion distribution from among the pre-processed data. The selected data may be provided to the output providing unit 124. The recognition data selection unit 123 may select some or all of the pre-processed data according to a preset criterion for predicting the lesion distribution. In addition, the recognition data selection unit 123 may select data according to a preset criterion by the learning by the model learning unit 114.

The output providing unit 124 may predict the lesion distribution after treatment of the subject by applying the selected data to the data recognition model. The output providing unit 124 may provide a recognition outcome according to a purpose of data recognition. The output providing unit 124 may apply the selected data to the data recognition model by using the data selected by the recognition data selection unit 123 as an input value. In addition, the recognition outcome may be determined by the data recognition model.

The model update unit 125 may update the data recognition model based on an evaluation of the recognition outcome provided by the output providing unit 124. For example, the model update unit 125 may provide the recognition outcome provided by the output providing unit 124 to the model learning unit 114 to allow the model learning unit 114 to update the data recognition model.

At least one of the data learning unit 110 and the data recognition unit 120 may be manufactured in a form of at least one hardware chip and mounted on an electronic device. For example, at least one of the data learning unit 110 and the data recognition unit 120 may be manufactured in a form of a dedicated hardware chip for artificial intelligence (AI), or may be manufactured as a part of an existing general-purpose processor (for example, a CPU or an application processor) or a graphic dedicated processor (for example, a GPU) to be mounted on various electronic devices described above.

Meanwhile, at least one of the data input unit 121, the pre-processing unit 122, the recognition data selection unit 123, the output providing unit 124, and the model update unit 125 in the data recognition unit 120 may be manufactured in a form of at least one hardware chip to be mounted on the electronic device. For example, at least one of the data input unit 121, the pre-processing unit 122, the recognition data selection unit 123, the output providing unit 124, and the model update unit 125 may be manufactured in a form of a dedicated hardware chip for artificial intelligence (AI), or may be manufactured as a part of an existing general-purpose processor (for example, a CPU or an application processor) or a graphic dedicated processor (for example, a GPU) to be mounted on the various electronic devices described above.

In this case, the data learning unit 110 and the data recognition unit 120 may be mounted on one electronic device, or may be mounted on separate electronic devices, respectively. For example, one of the data learning unit 110 and the data recognition unit 120 may be included in the electronic device, and the other may be included in the server. In addition, the data learning unit 110 and the data recognition unit 120 may provide model information built by the data learning unit 110 to the data recognition unit 120 through wired or wireless communication, or the data input into the data recognition unit 120 may be provided, as additional learning data, to the data learning unit 110.

The output unit 200 may display or output information processed by the prediction device 10. The output unit 200 may include a user interface for receiving the brain image data and a display unit for displaying an outcome of the prediction of the lesion distribution (output image data) or the like. A user may determine a method for treatment, such as whether or not to perform recanalization treatment for the subject by referring to the outcome of the prediction of the lesion distribution displayed on the output unit 200.

Particularly, the output unit 200 may generate the output image data including information on the lesion distribution after recanalization treatment for the subject by using the prediction model. The output image data is generated by the output providing unit 124 of the data recognition unit 120, and the output unit 200 may receive and output data from the output providing unit 124.

The output unit 200 may generate the first output image data through the success prediction model and generate the second output image data through the failure prediction model. The first output image data may include information on the lesion distribution after the successful recanalization treatment for the subject, and the second output image data may include information on the lesion distribution after the unsuccessful recanalization treatment for the subject.

The output unit 200 may compare the first and second output image data with each other to determine a treatment policy, such as whether or not to perform the recanalization treatment for the subject.

Figure 3:
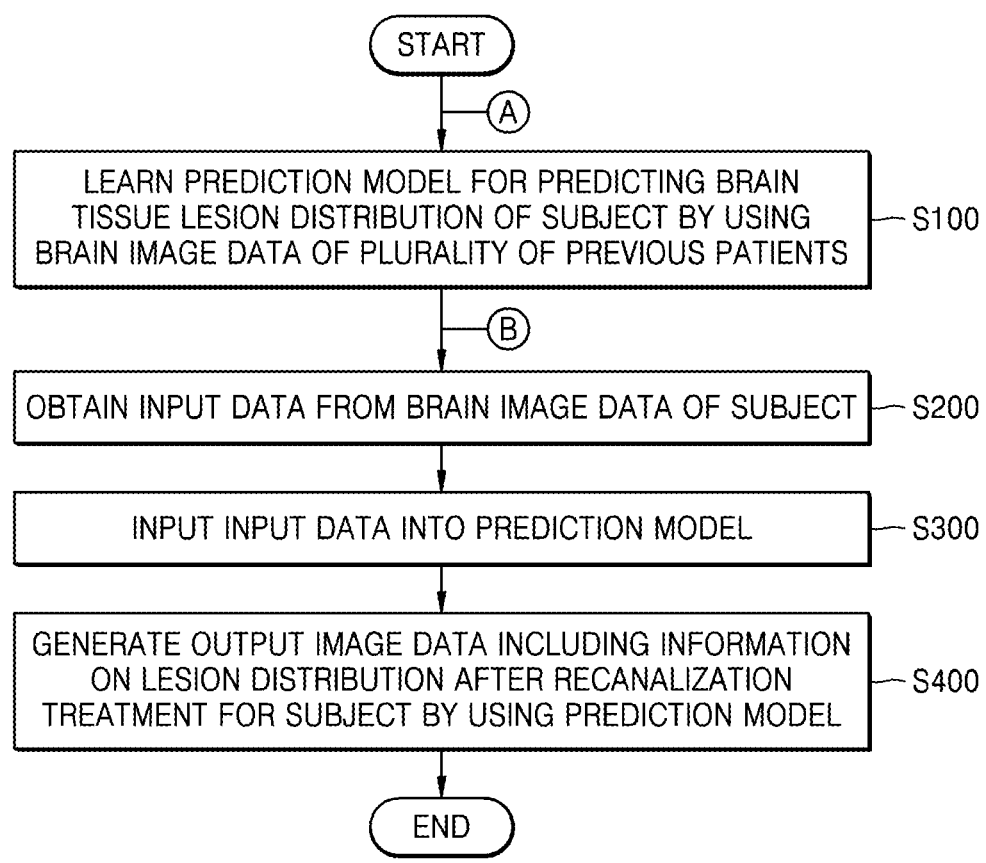
FIG. 3 is a flowchart illustrating a method of predicting a lesion distribution according to an embodiment of the present disclosure.

FIG. 3 is a flowchart illustrating the method of predicting the lesion distribution according to an embodiment of the present disclosure. The method (hereinafter, may be referred to as a 'prediction method') for predicting the lesion distribution according to an embodiment includes a model learning operation S100, an input obtaining operation S200, an input operation S300, and an output operation S400.

The model learning operation S100 of learning the prediction model for predicting the distribution of the brain tissue lesion of the subject by using the brain image data of the plurality of previous patients may be performed. The operation S100 may be performed by the control unit 100 of the prediction device 10, and among others, the data learning unit 110. The prediction model of the present disclosure may include the success prediction model SR and the failure prediction model UR that are classified according to whether or not the recanalization treatment succeeds for the data provider or the subject. The two prediction models SR and UR will be described in more detail with reference to FIGS. 5 to 8 to be described below.

The operation S100 will be described in more detail in FIG. 4 to be described below.

The input obtaining operation S200 of obtaining the input data from the brain image data of the subject may be performed. The operation S200 may be performed by the data recognition unit 120 of the control unit 100. Particularly, the operation S200 may be performed by at least one of the data input unit 121, the pre-processing unit 122, and the recognition data selection unit 123 of the data recognition unit 120.

The input operation S300 of inputting the input data into the prediction model may be performed. In this case, the input data input into the prediction model may be data which is obtained by performing data pre-processing by the pre-processing unit 122 on the brain image data of the subject before treatment received by the data input unit 121, and is finally selected by the recognition data selection unit 123. For the input data, the data processing algorithm for the 'learning input data' described above may be applied in the same manner. The prediction model may be a configuration element corresponding to the model learning unit 114 of the data learning unit 110.

The output operation S400 of generating the output image data including information on the lesion distribution after treatment for the subject may be performed by using the prediction model. The treatment may be the recanalization treatment. The operation S400 may be performed by the control unit 100 and the output unit 200. Particularly, the output image data may be generated through the output providing unit 124 of the data recognition unit 120 by using the prediction model learned by the model learning unit 114, and the output image data may be displayed through the output unit 200.

The operation S400 may include a first output operation of generating first output image data including information on the lesion distribution after successful recanalization treatment for the subject by inputting the input data into the success prediction model, and a second output operation of generating second output image data including information on the lesion distribution after unsuccessful recanalization treatment for the subject by inputting the input data into the failure prediction model.

The operation S400 may further include an operation of comparing the first output image data and the second output image data to each other to determine the treatment policy, such as whether or not to perform the recanalization treatment for the subject.

Figure 4:
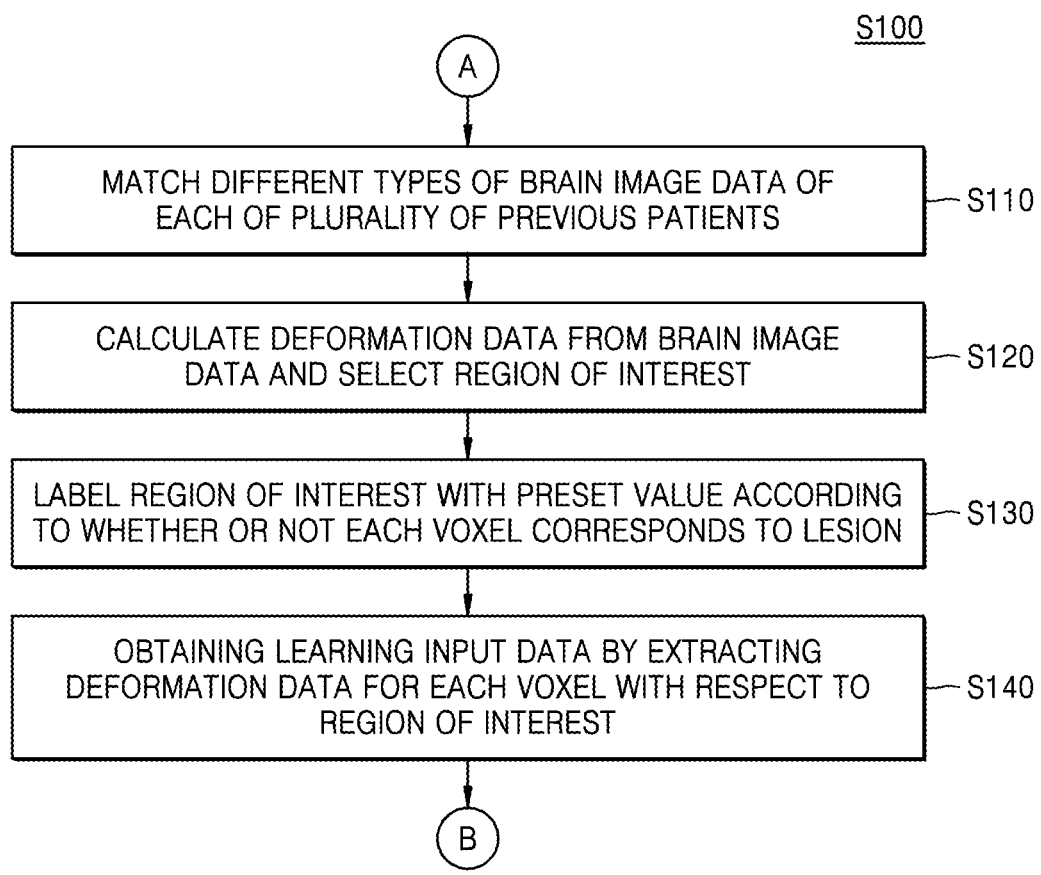
FIG. 4 is a detailed flowchart illustrating an operation of the method of predicting a lesion distribution according to an embodiment of the present disclosure.

FIG. 4 is a more detailed flowchart illustrating the model learning operation S100 of the method of predicting the lesion distribution according to an embodiment of the present disclosure. The operation S100 may include operations to be described below.

An image matching operation S110 of matching different types of the brain image data of each of the plurality of previous patients may be performed. The different types of brain image data that are matched to each other in the image matching operation may include first diffusion weighted image (DWI) data obtained before treatment, perfusion weighted image (PWI) data before treatment, and second diffusion weighted image (DWI) data obtained after treatment.

Thereafter, an operation S120 of calculating the deformation data from the brain image data and selecting the region of interest may be performed. The deformation data calculated for each type of the brain image data may be different and particularly, the ADC may be calculated from the DWI data before treatment and the TTP or the rTTP may be calculated from the PWI data. The interest region and the symmetric region may be selected from the DWI data before treatment, and the PWI data before treatment, and the region of interest may be selected from the DWI data after treatment.

Thereafter, a labeling operation S130 of labeling the region of interest with a preset value (for example, 0 or 1) according to whether or not each voxel corresponds to the lesion may be performed. The labeling operation may be performed on the second DWI data.

Thereafter, a learning input obtaining operation S140 of obtaining the learning input data by extracting the deformation data for each voxel with respect to the region of interest and the symmetric region may be performed.

The above-described operations S110, S120, S130, and S140 may be performed by the data recognition unit 110, and more particularly, may be performed by the data pre-processing unit 112. According to an embodiment, the image matching operation S110 may be performed by the data input unit 111.

Figure 5:
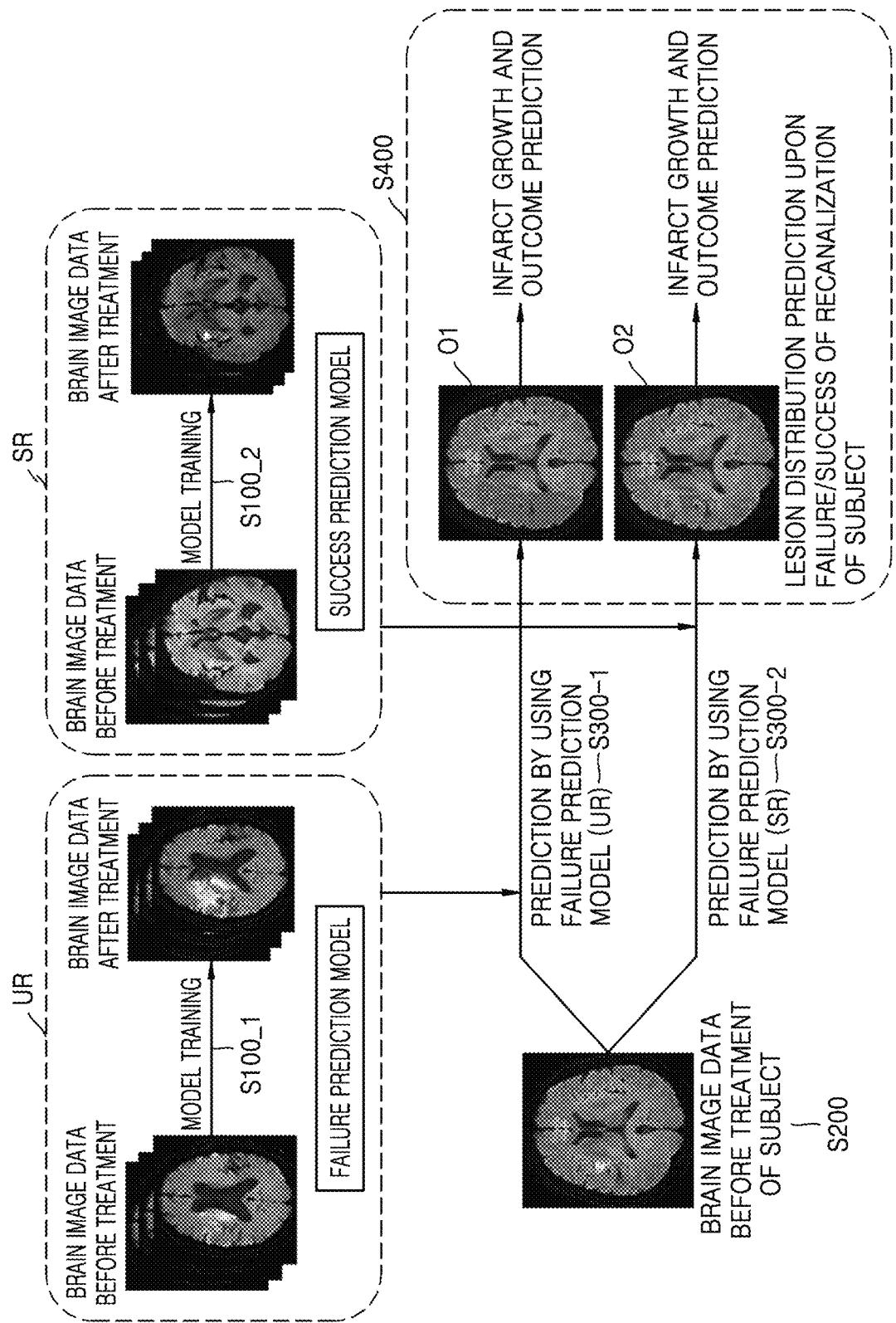
FIG. 5 is a conceptual diagram illustrating an input/output operation of the method of predicting a lesion distribution according to an embodiment of the present disclosure.

FIG. 5 is a conceptual diagram illustrating an input/output operation of the method of predicting the lesion distribution according to an embodiment of the present disclosure.

The prediction model of the present disclosure includes the success prediction model SR and the failure prediction model UR. Each of the two prediction models SR and UR may be learned by using the brain image data before and after treatment of the plurality of previous patients. In each block of the prediction models UR and SR, a left side is the brain image data before treatment, and a right side is the brain image data after treatment. The model learning operation S100 of the method of predicting the lesion distribution of the present disclosure may include an operation (S100-1) of learning the failure prediction model UR and an operation (S100-2) of learning the success prediction model SR.

As an index used as a measure to determine whether or not to perform the recanalization of the blood vessels, there is a modified treatment in cerebral infarction (mTICI) index. The mTICI index may sequentially have values of 0, 1, 2a, 2b, and 3. The success prediction model SR of the present disclosure may be learned based on the data of the previous patients with the mTICI indexes of 2b and 3 (mTICI≥2b), and may be learned based on the data of the previous patients with the mTICI indexes of 0, 1, and 2a (mTICI≤2a).

The control unit 100 of the prediction device 10 of the present disclosure may receive the brain image data before treatment of the subject to predict the lesion distribution. For the brain image data before treatment, the operation S200 of obtaining the input data by pre-processing the data to be used for predicting the lesion distribution by using the above-described prediction model may be performed.

The processed input data may be input into each of the success/failure prediction models SR and UR (operations S300-1, S300-2, and S300), and the lesion distribution of the subject may be predicted through each input model.

Output image data O1 and O2 may be output through the output unit 200 of the prediction device 10 to predict the distribution of the brain tissue lesion of the subject. At this time, by outputting the output, in a form of image data, by using a machine-learned prediction model based on actual treatment success/failure cases, there is a merit of providing accurate and intuitive prediction information to the user (subject, tester, or the like).

In a case where the input data of the subject is input into the failure prediction model UR, the output unit 200 may output the first output image data O1 including information on the lesion distribution predicted when the recanalization treatment for the subject fails. In a case where the input data of the subject is input into the success prediction model SR, the output unit 200 may output the second output image data O2 including information on the lesion distribution predicted when the recanalization treatment succeeds. A degree and outcome of an infarct growth may be predicted through the output image data O1 and O2.

Figure 6:
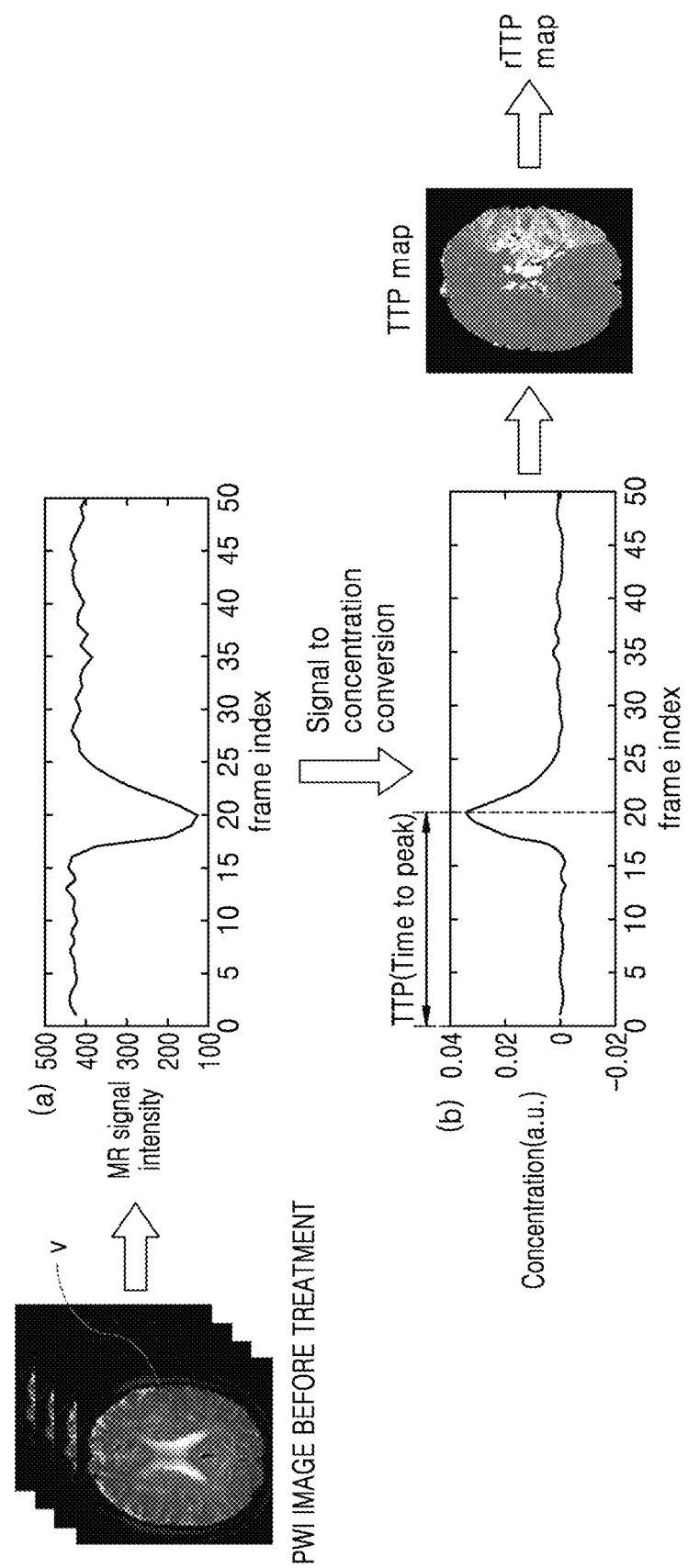
FIG. 6 is a conceptual diagram illustrating a method of generating an rTTP map according to an embodiment of the present disclosure.

FIG. 6 is a conceptual diagram illustrating a method of generating the rTTP map according to an embodiment of the present disclosure.

In an upper left of FIG. 6, each frame of the PWI image data before treatment of the data provider is illustrated. First, as illustrated in a graph (a) of FIG. 6, an MR signal intensity for each voxel v for each frame (it may be a frame by time) of the PWI image data is obtained. Thereafter, as illustrated in a graph (b) of FIG. 6, the MR signal intensity is converted into a contrast agent concentration, and the TTP for each voxel v may be calculated on the concentration graph of (b) to obtain a TTP map. The TTP refers to a time when the concentration of the contrast agent is greatest. At this time, a formula for converting the MR signal intensity to the concentration of the contrast agent is as illustrated in the following [Equation 1].

$$C(t) = -\frac{1}{r_2 \cdot TE} \cdot \log\left(\frac{S(t)}{S_0}\right) \quad \text{[Equation 1]}$$

In Equation 1, C(t) is the concentration of the contrast agent, $r_2$ is a T2 relaxivity, TE is an echo time, S(t) is a signal intensity of the magnetic resonance imaging, and $S_0$ is an initial value of the signal intensity of the magnetic resonance imaging. The time to peak (TTP) value may be determined at a time point when the concentration (C(t)) of the contrast agent on the left side is greatest.

Thereafter, a median of the TTP value for each voxel is calculated for the non-lesion normal site (contralateral region in FIG. 6) from the TTP map, and then the median may be subtracted from the TTP value of the lesion site to obtain the rTTP map. The relative time to peak (rTTP) is data that refers to a time when the concentration of the contrast agent in the PWI image is greatest, that is, the signal of the magnetic resonance imaging is smallest, and a relative difference in the arrival time to the greatest concentration of the contrast agent in the lesion site compared to the normal site may be presented. For voxels having (x, y) coordinate values, the process of obtaining the rTTP described above is expressed as in the following [Equation 2].

$$rTTP(x,y)=TTP(x,y)-\text{median}(TTP \text{ of normal zone}) \quad \text{[Equation 2]}$$

Figure 7:
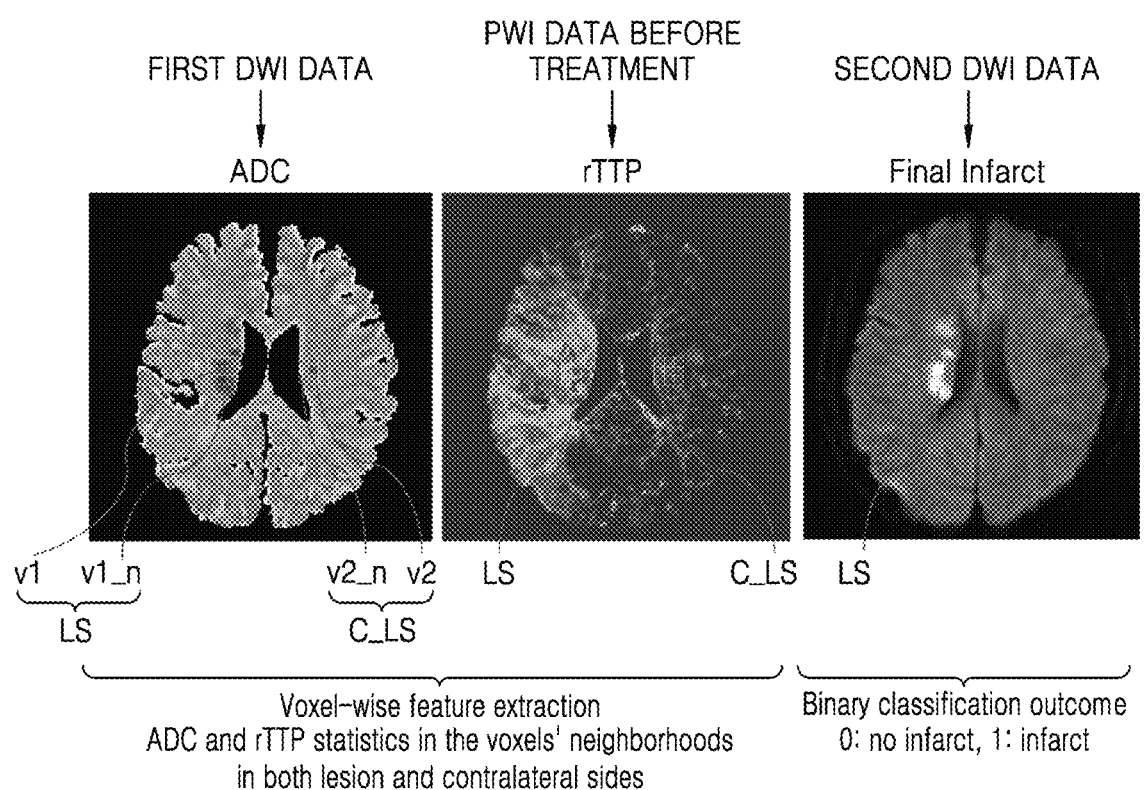
FIG. 7 is a conceptual diagram illustrating a data pre-processing operation according to an embodiment of the present disclosure.

FIG. 7 is a conceptual diagram illustrating a method of obtaining the input data for machine learning of the prediction model as a data pre-processing operation according to an embodiment of the present disclosure.

Referring to FIG. 7, as the brain image data used to predict the lesion distribution according to the present disclosure, the first DWI data (DWI data before treatment), the PWI data before treatment, and the second DWI data (DWI data after treatment) are illustrated.

A method of calculating the rTTP from the PWI data before treatment illustrated in a center of FIG. 7 is described above in the portion related to FIG. 6.

An apparent diffusion coefficient (ADC) may be calculated from the first DWI data. The ADC is an index that may determine a degree of diffusion of water molecules due to lesion or cell death in the brain tissue, that is, a degree of restriction of diffusion of water molecules. The ADC represents a change in signal intensity of DWI images having b values different from each other.

First, the region of interest LS corresponding to the lesion site and the symmetric region C_LS corresponding to the normal site may be selected for the first DWI data. In this case, the voxel in the region of interest LS may include a first central voxel v1 and a first peripheral voxel v1_n. The first peripheral voxel v1_n may be selected within a 5×5×3 region based on the first central voxel v1 but is not limited thereto. Similarly, the voxel in the symmetric region C_LS may include a second central voxel v2 and a second peripheral voxel v2_n. The second peripheral voxel v2_n may be selected within a 5×5×3 region based on the second central voxel v2 but is not limited thereto.

Statistical information of each value may be extracted (voxel-wise feature extraction) by calculating an ADC value and an rTTP value for each voxel of the region of interest LS and the symmetric region C_LS.

From the second DWI data, it may be determined whether or not the voxel in the region of interest LS corresponds to a final brain injury lesion. That is, each voxel may be labeled with a preset value according to whether or not each voxel corresponds to the lesion. The preset value may be 0 or 1, and for example, if the voxel corresponds to the lesion (infarct), the preset value may be labeled as a value of 1, and the voxel does not correspond to the lesion (no infarct), the preset value may be labeled as a value of 0. At this time, there may be a voxel that is determined not to correspond to the lesion and labeled as the value of 0 even within the region of interest LS, and a voxel that is determined to correspond to the lesion and labeled as the value of 1 may exist even within the symmetric region C_LS. However, in a case of a patient with hyperacute cerebral infarction, since a probability of the lesion occurring only in one brain is high, in general, there may be the voxel labeled as 1 in the region of interest LS, and there may be a low possibility that the voxel labeled as 1 exists in the symmetric region C_LS.

Even for the voxels in different positions and the voxels for image data of different slices, the input data (training data) for learning/training the prediction model of the present disclosure may be obtained by applying the above-described algorithm.

The following [Table 1] may be an example of the format of the input data obtained based on the foregoing description. The number in a left column may indicate the identification number assigned to the voxel, and statistical values of a lower limit value (min), a upper limit value (max), and an average value (mean) of each of the ADC and rTTP values of the lesion region (lesion) and the symmetric region (contra) may be extracted in the form of the following [Table 1], and the [Table 1] may be used as an input vector (feature vector) for the machine learning.

In the following [Table 1], other deformation data indicated by . . . may be any one selected from a standard deviation, a kurtosis, a skew, a 10 percentile, a 25 percentile, a 75 percentile, and a 90 percentile, but is not limited thereto.

Figure 8:
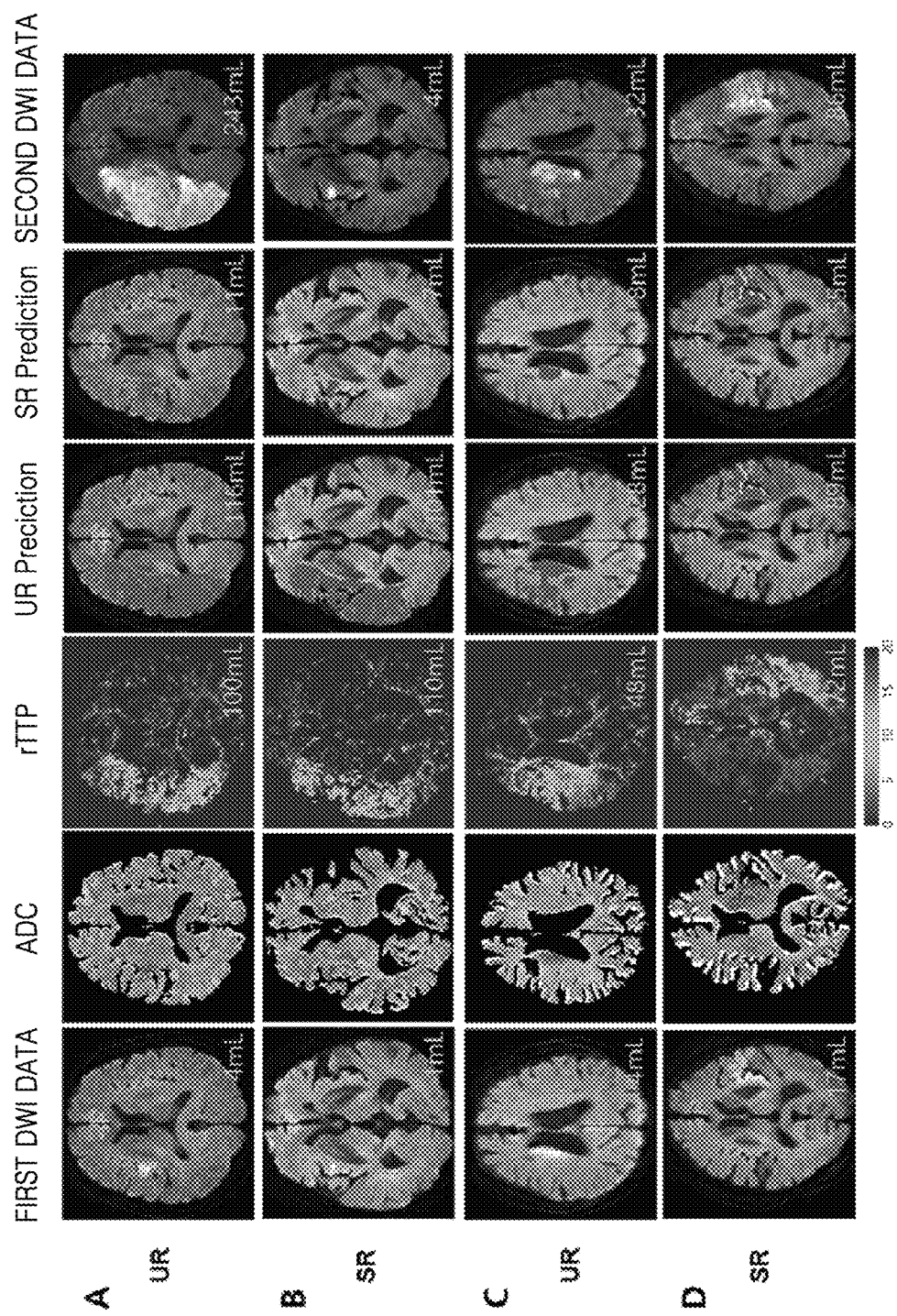
FIG. 8 is a diagram illustrating an outcome of predicting lesion distributions in a plurality of subjects by using a prediction model according to an embodiment of the present disclosure.

Referring to FIG. 8, the outcomes of the prediction of the lesion distribution by applying the success/failure prediction models for 4 subjects are compared and illustrated. Cases A and C illustrated on the left side of FIG. 8 are cases of patients in which the recanalization treatment fails, and Cases B and D are cases of patients in which the recanalization treatment is successful. As indicated on the upper side of FIG. 8, the image data illustrated in each column indicates the first DWI data, the ADC, the rTTP, the prediction outcome (UR Prediction) using the failure prediction model UR, the prediction outcome (SR prediction) using the success prediction model SR, and the second DWI data sequentially from the left column. In this case, the second DWI data may represent DWI data after 7 days of the recanalization treatment. In the present disclosure, the reason that the second DWI data is exemplified as data after 7 days may be because the lesion distribution after 7 days has a high correlation with a long-term prognosis of the lesion distribution. The ADC may be data extracted from the first DWI data, and the rTTP may be data extracted from the PWI data before treatment to be described above. The prediction models UR and SR may be machine learned based on the ADC, the rTTP, and the second DWI data. The number on the lower right of each image data indicates a volume of the lesion site in the brain tissue.

First, the case A (failure, a case where the infarct growth is also large) will be described. When comparing and explaining the DWI data before and after treatment in the case A, the lesion volume before treatment was 4 ml in the first DWI data and the lesion volume after treatment was 243 ml in the second DWI data, and thereby, the case A corresponds to a case where the infarct growth (or lesion growth) is as large as approximately 240 ml.

Here, as an outcome of the prediction of the lesion distribution from the data (ADC and rTTP) before treatment of the patient of the case A by using the failure prediction model UR, it may be confirmed that the lesion volume is approximately 116 ml, that is, the infarct growth is predicted as high as approximately 112 ml (value obtained by subtracting the lesion volume before treatment from the lesion

TABLE 1

| sample | Extracted features from baseline DWI and PWI ||||||||||||| Tissue Outcome from day 7 DWI |
|---|---|---|---|---|---|---|---|---|---|---|---|---|---|---|
| | Lesion ADC min | Lesion ADC max | Lesion ADC mean | ... | Contra. ADC min | Contra. ADC max | Contra. ADC mean | Lesion rTTP min | Lesion rTTP max | Lesion rTTP mean | ... | Contra. rTTP min | Contra. rTTP max | Contra. rTTP mean | ... | whether or not final infarct |
| 1 | | | | | | | | | | | | | | | | 1 |
| 2 | | | | | | | | | | | | | | | | 0 |
| 3 | | | | | | | | | | | | | | | | 1 |
| ... | | | | | | | | | | | | | | | | ... |
| N − 1 | | | | | | | | | | | | | | | | 0 |
| N | | | | | | | | | | | | | | | | 0 |

As described above, after obtaining the input data extracted from the brain image data of each of the plurality of previous patients, the success/failure prediction models of the present disclosure may be learned to calculate a final trained prediction model.

FIG. 8 is a diagram illustrating outcomes of the prediction of the lesion distribution of the plurality of subjects by using the prediction model according to an embodiment of the present disclosure.

volume of the UR prediction). On the other hand, a case of the prediction by using the success prediction model SR, the lesion volume was predicted to be approximately 11 ml.

Next, the case B (success, a case where the infarct growth is also small) will be described. When comparing and explaining the DWI data before and after treatment of the case B, the lesion volume before treatment is 1 ml in the first DWI data and the lesion volume after treatment is 4 ml in the second DWI data, and thereby, the case B corresponds to a case where the infarct growth is as small as approximately 3 ml.

Here, as an outcome of the prediction of the lesion distribution from the data (ADC and rTTP) before treatment of the patient of the case B by using the success prediction model SR, it may be confirmed that the lesion volume is approximately 7 ml, that is, the infarct growth is predicted as low as approximately 6 ml (value obtained by subtracting the lesion volume before treatment from the lesion volume of the SR prediction). On the other hand, in a case of the prediction by using the failure prediction model UR, the lesion volume was predicted to be approximately 101 ml.

Next, the case C (failure, a case where the infarct growth is also small) will be described. When comparing and explaining the DWI data before and after treatment of the case C, the lesion volume before treatment is 4 ml in the first DWI data and the lesion volume after treatment is 32 ml in the second DWI data, and thereby, the case C corresponds to a case where the infarct growth is as small as approximately 28 ml.

Here, as an outcome of the prediction of the lesion distribution from the data (ADC and rTTP) before treatment of the patient of the case C by using the failure prediction model UR, it may be confirmed that the lesion volume is approximately 28 ml, that is, the infarct growth is predicted as low as approximately 22 ml. On the other hand, in a case of the prediction by using the success prediction model SR, the lesion volume was predicted to be approximately 8 ml.

Next, the case D (success, a case where the infarct growth is also large) will be described. When comparing and explaining the DWI data before and after treatment of the case D, the lesion volume before treatment is 17 ml in the first DWI data and the lesion volume after treatment is 86 ml in the second DWI data, and thereby the case D corresponds to a case where the infarct growth is as large as approximately 69 ml.

Here, as an outcome of the prediction of the lesion distribution from the data (ADC and rTTP) before treatment of the patient of the case D by using the success prediction model SR, it may be confirmed that the lesion volume is approximately 55 ml, that is, the infarct growth is predicted as large as approximately 38 ml. On the other hand, in a case of the prediction by using the failure prediction model UR, the lesion volume was predicted to be approximately 89 ml.

Considering the cases A and C, which are cases where the recanalization treatment failed, it may be confirmed that the tendency was relatively accurately predicted through the failure prediction model UR of the present disclosure for each case where the infarct growth was large or small upon failure. Likewise, considering the cases B and D, which are cases where the recanalization treatment succeeded, it may be confirmed that the tendency was relatively accurately predicted through the success prediction model SR of the present disclosure for each case where the infarct growth was large or small upon success.

As described above, according to the method of predicting the lesion distribution according to an embodiment of the present disclosure, through the success and failure prediction models separately machine-learned by using the brain image data when the treatment of the subject succeeds or fails for the data provider or the subject, there is an merit of being able to accurately and intuitively predict the lesion distribution after treatment, upon the success or the failure, from the data before treatment of the subject. Accordingly, the success rate and safety of cerebral infarction treatment for the subject may be improved.

In more detail, the DWI and the PWI data may be used as the brain image data used for prediction, and the ADC, the TTP, and the rTTP may be used as the deformation data extracted from the brain image data, so that it is possible to increase the accuracy of the prediction of the lesion distribution in case of the success and/or failure of the recanalization treatment for each subject.

In addition, prediction information on accurate and intuitive lesion distribution and the volume may be provided by using only the image data through the prediction model learned from actual treatment success/failure case data. There is a merit of being able to perform the diagnosis through visual information/foundation regarding the decision of the treatment policy for the subject (patient) or a caregiver.

Figure 9:
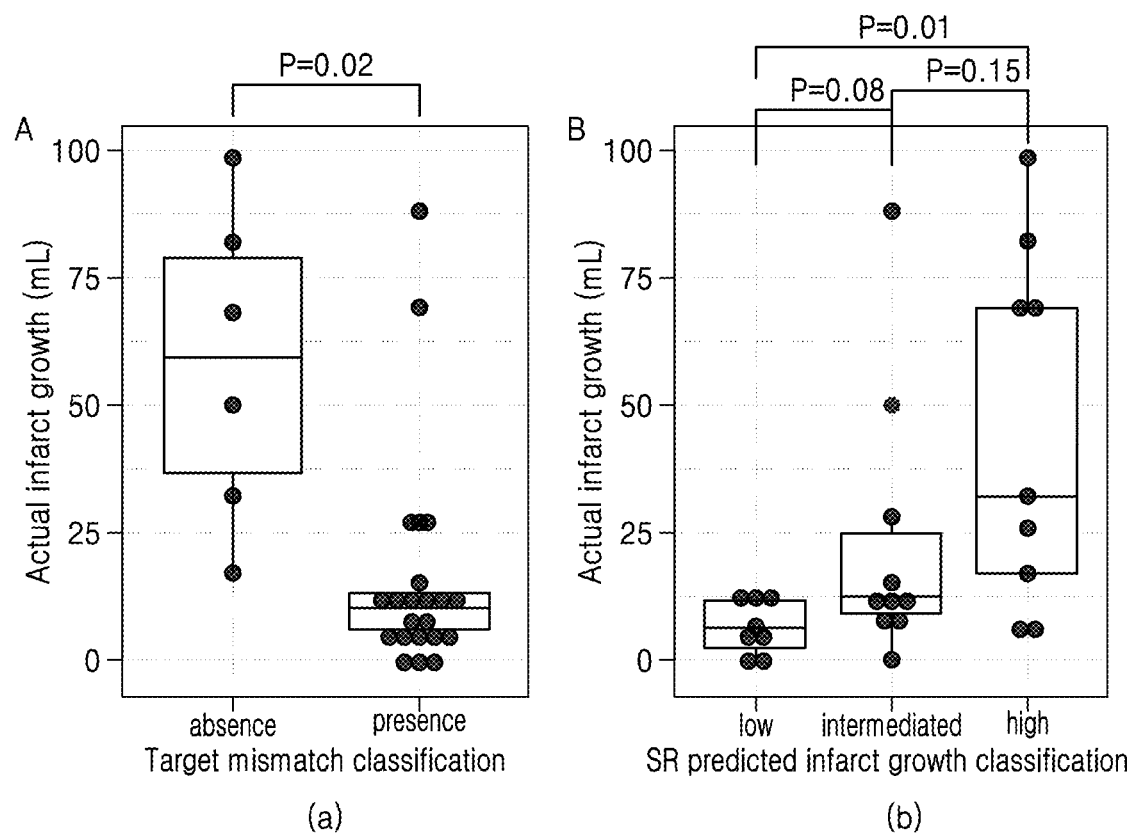
FIG. 9 shows graphs illustrating statistical significance of a method of predicting a lesion distribution according to an embodiment of the present disclosure.

FIG. 9 is a graph illustrating statistical significance of the method of predicting the lesion distribution according to an embodiment of the present disclosure. FIG. 9 is graphs of cases, where the lesion distribution is predicted by the success prediction model SR for the subjects of the treatment success case, is grouped according to an actual infarct growth volume (ml). FIG. 9(a) is a graph (in a case of P=0.02) where the subjects are classified by a target mismatch method, and FIG. 9(b) is a graph (in a case of P=0.01) where the subjects are classified based on the infarct growth volume predicted by using the prediction model of the present disclosure. A vertical axis of each graph represents the actual infarct growth volume (ml).

Hereinafter, the P value may be a measure representing a difference in a patient distribution between groups grouped in each of the methods (a) and (b). For example, if the P value is less than or equal to approximately 0.05, the P value may be referred to as having statistical significance. Meanwhile, dots illustrated in each graph indicate the number of patients, and hereinafter may be expressed as 'n'. The target mismatch method may refer to a method of calculating the lesion region of each of the DWI data and the PWI data and a degree of mismatch between the lesion regions. In this case, it may be interpreted that the higher the calculated target mismatch degree, the better the degree of improvement is when recanalization is successful.

First, referring to FIG. 9(a), in a case where grouping is performed by using the existing target mismatch method, a mismatch absence group illustrates a heterogeneous distribution with respect to the vertical axis, but the number of patients indicated by the dots is very small (n=6) compared to a group (mismatch presence) illustrating the mismatch. Therefore, it may be confirmed to be difficult to determine that there is a statistically significant difference in the infarct growth when the mismatch absence group is compared with the mismatch presence group.

On the other hand, referring to FIG. 9(b), the infarct growth volume is classified into a low group, an intermediate group, and a high group, and grouped according to the infarct growth volume corresponding to each case. At this time, it may be confirmed that the low group (n=8) and the high group (n=9) have statistical significance. The high group (SR-predicted infarct growth≥35 ml) illustrates a non-uniform distribution along the vertical axis, while the low group (SR-predicted infarct growth<15 ml) illustrates a narrow distribution.

As described above, when predicting the lesion distribution and the volume by using the prediction model according to the present disclosure, it is possible to grasp the tendency of the lesion distribution and the volume to a large or small degree upon the success or failure of the recanalization treatment.

Figure 10:
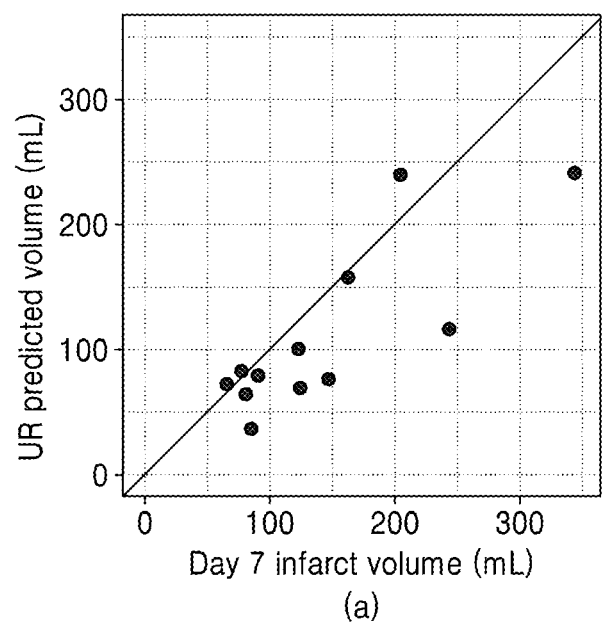
FIG. 10 shows graphs illustrating prediction characteristics of a failure prediction model on patients with unsuccessful recanalization and a success prediction model on patients with successful recanalization according to an embodiment of the present disclosure.
Figure 10:
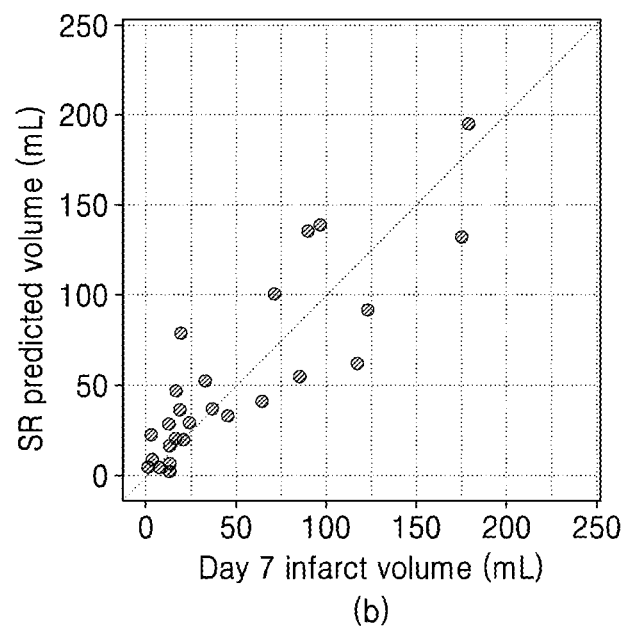

FIG. 10 is graphs illustrating prediction characteristics of the success prediction model SR and the failure prediction model UR according to an embodiment of the present disclosure. In FIGS. 10(a) and 10(b), a horizontal axis illustrates the final infarct volume (mL) manually measured after dividing the lesion region on the second DWI data (day-7 DWI data), and a vertical axis Illustrates the final infarct volume (mL) predicted by the prediction model of the present disclosure. FIG. 10(a) is an outcome of the failure prediction model UR and FIG. 10(b) is an outcome of the success prediction model SR.

As an outcome of calculating a value of an intraclass correlation coefficient (hereinafter referred to as 'ICC') by using the above-described value of the horizontal axis as a reference value, in the case of FIG. 10(a), ICC=0.73 (95% confidence interval is 0.31 to 0.91, and P<0.01), and in the case of FIG. 10(b), ICC=0.87 (95% confidence interval is 0.73 to 0.94, and P<0.001). It may be confirmed that the correlation is large between the infarct region directly calculated from the second DWI data and the infarct region predicted by using the prediction models SR and UR of the present disclosure through the distribution and the ICC value on the graph of FIG. 10.

Hereinafter, an outcome of measuring the match of the lesion distribution, in which the horizontal axis and the vertical axis of FIG. 10 are illustrated in a form of a binary mask, will be described by using a dice similarity coefficient (DSC).

In a case of an external validation of all patient samples, a median DSC score was calculated to be approximately 0.49 and an interquartile range (hereinafter referred to as 'IQR') was calculated to be approximately 0.37 to approximately 0.59. In the case of the external verification by the failure prediction model UR, the median DSC score is calculated to be approximately 0.58 (IQR is approximately 0.55 to approximately 0.67), and in the case of the external verification by the success prediction model SR, the median DSC score is calculated to be approximately 0.43 (IQR is approximately 0.20 and to 0.52), and thus, it may be confirmed that the DSC value of the case where the recanalization treatment is successful is smaller. In a case where the final infarct volume is small, the DSC value also tends to decrease, and as described above, both models UR and SR may be confirmed by separately calculated values.

Figure 11:
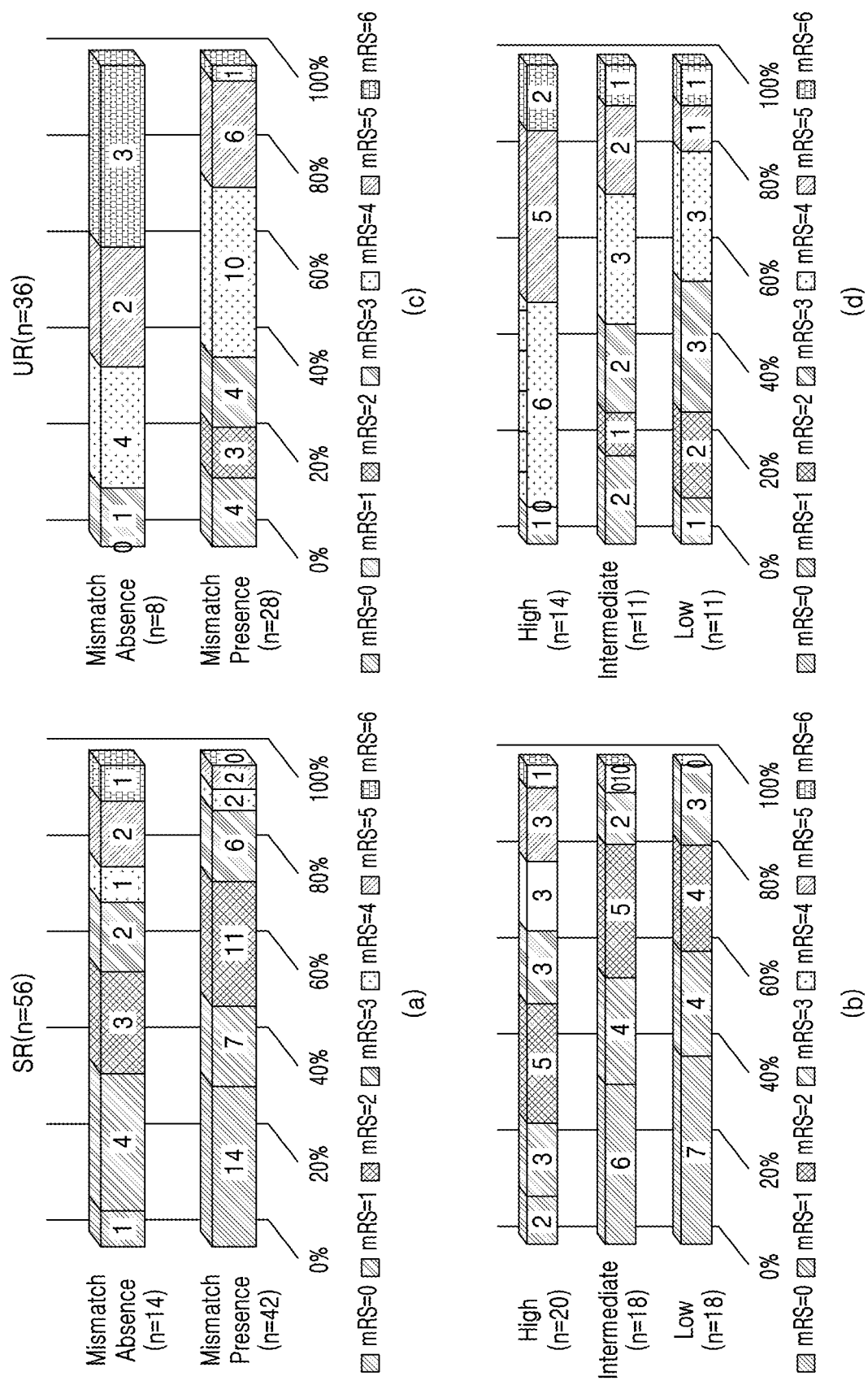
FIG. 11 is a diagram illustrating a distribution of a clinical prognostic score outcome according to a method of predicting a lesion distribution according to an embodiment of the present disclosure.

FIG. 11 is diagrams illustrating an outcome distribution of a clinical prognostic score according to the method of predicting the lesion distribution according to an embodiment of the present disclosure. FIGS. 11(a) and 11(b) are diagrams for a patient group who succeeded in the recanalization treatment, and FIGS. 11(c) and 11(d) are diagrams for a patient group who failed the treatment. FIGS. 11(a) and 11(c) are diagrams illustrating an outcome distribution of grouping for a target mismatch method. FIGS. 11(b) and 11(d) are diagrams illustrating an outcome distribution of the clinical prognostic score for each group after grouping into three groups according to the degree of predicted infarct growth volume by the prediction method according to the present disclosure.

In general, in the measurement of the prognosis, a modified Rankin scale (mRS) value after 90 days of symptom onset may be used, and it may be interpreted that the higher the mRS value, the worse the prognosis is. Referring to FIGS. 11(b) and 11(d), in a case of a group (Low) in which the infarct growth is predicted to be small, it may be confirmed that the prognosis tends to be good compared to a group (High) that is predicted to be large. For example, it is assumed that the mRS value of 2 or less has a good prognosis. Referring to FIG. 11(b), it may be confirmed that the number of patients with a good prognosis is approximately 80% in the case of the low group (Low) and approximately 50% in the case of the high group (High).

The embodiments according to the present disclosure described above may be implemented in a form of a computer program that may be executed through various configuration elements on a computer, and such a computer program may be recorded in a computer-readable medium. In this case, a medium may store a program executable by a computer. Examples of media may include a magnetic medium such as a hard disk, a floppy disk, or a magnetic tape, an optical recording medium such as a CD-ROM or a DVD, a magneto-optical medium such as a floptical disk, a ROM, a RAM, a flash memory, and the like to be configured to store program instructions.

Meanwhile, the computer program may be specially designed and configured for the present disclosure or may be known and usable to those skilled in the computer software field. Examples of the computer program may include not only a machine language code produced by a compiler but also a high-level language code that may be executed by a computer by using an interpreter or the like.

According to the embodiments of the present disclosure, success and failure prediction models are separately learned based on the brain image data before and after treatment, and in a case where the treatment successes or fails from data before treatment of the subject by using the two prediction models, the lesion distribution and the volume are compared and predicted, and thus, it is possible to provide a criterion for determining the treatment policy.

Accordingly, a success rate and safety of the cerebral infarction treatment for the subject may be improved.

In addition, accurate and intuitive prediction information on the lesion distribution and the volume may be provided by using only the image data through the prediction model learned from actual treatment success/failure case data. There is a merit of being able to perform diagnosis through the visual information/foundation regarding the decision of the treatment policy for the subject (patient) or a caregiver.

It should be understood that examples described herein should be considered in a descriptive sense only and not for purposes of limitation. Descriptions of features or aspects within each example should typically be considered as available for other similar features or aspects in other examples. While one or more examples have been described with reference to the figures, it will be understood by those of ordinary skill in the art that various changes in form and details may be made therein without departing from the spirit and scope of the disclosure as defined by the following claims.

What is claimed is:

1. A method of predicting a brain tissue lesion distribution, the method comprising:
  a model learning operation of learning a prediction model for predicting a brain tissue lesion distribution in a subject by using brain image data of a plurality of previous patients, wherein the model learning operation includes an image matching operation of matching different types of the brain image data of each of the plurality of previous patients, an operation of calculating deformation data from the brain image data and selecting a region of interest corresponding to the lesion site, an operation of labeling the region of interest with a preset value according to whether or not each voxel corresponds to a lesion and a learning input obtaining operation of obtaining learning input data by extracting the deformation data for each voxel with respect to the region of interest;
an input obtaining operation of obtaining input data from brain image data of the subject;
an input operation of inputting the input data into the prediction model; and
an output operation of generating output image data including information on the lesion distribution after recanalization treatment for the subject, by using the prediction model,
wherein the prediction model includes a success prediction model that is learned using pre-treatment and post-treatment brain image data of a plurality of first patients who have modified Treatment In Cerebral Infarction (mTICI) scores of 2b and 3 among the plurality of previous patients, and a failure prediction model that is learned using pre-treatment and post-treatment brain image data of a plurality of second patients who have mTICI scores of 0, 1 and 2a among the plurality of previous patients,
wherein the brain image data matched in the image matching operation includes first diffusion weighted image (DWI) data obtained before treatment, perfusion weighted image (PWI) data before treatment, and second diffusion weighted image (DWI) data obtained after treatment, and
wherein the calculating and selecting operation includes
an operation of calculating an apparent diffusion coefficient (ADC) from the first diffusion weighted image (DWI) data;
an operation of calculating relative time to peak (rTTP) from the perfusion weighted image (PWI) data before treatment to obtain an rTTP map; and
an operation of selecting the region of interest from the first diffusion weighted image (DWI) data, the perfusion weighted image (PWI) data before treatment, and the second diffusion weighted image (DWI) data.

2. The method of predicting a brain tissue lesion distribution of claim 1, wherein the model learning operation further includes
an operation of selecting a symmetric region corresponding to a normal site from the brain image data; and
an operation of extracting the deformation data for each voxel with respect to the symmetric region to obtain the learning input data, and
wherein the symmetric region is selected for the first diffusion weighted image (DWI) data and the perfusion weighted image (PWI) data before treatment.

3. The method of predicting a brain tissue lesion distribution of claim 1, wherein the output operation includes
a first output operation of inputting the input data into the failure prediction model to generate first output image data including information on the lesion distribution after failure of the recanalization treatment for the subject; and
a second output operation of inputting the input data into the success prediction model to generate second output image data including information on the lesion distribution after success of the recanalization treatment for the subject.

4. The method of predicting a brain tissue lesion distribution of claim 3, wherein the output operation further includes an operation of comparing the first output image data and the second output image data to determine whether or not the recanalization treatment is to be performed.

5. A device for predicting a brain tissue lesion distribution, the device comprising:
a control unit and an output unit in a device for predicting a brain tissue lesion after treatment of a subject,
wherein the control unit
learns a prediction model for predicting a brain tissue lesion distribution of the subject by using brain image data of a plurality of previous patients,
matches different types of brain image data of each of the plurality of previous patients,
calculates deformation data from the brain image data and selects a region of interest corresponding to a lesion site,
labels the region of interest with a preset value according to whether or not each voxel corresponds to a lesion,
obtains learning input data by extracting the deformation data for each voxel with respect to the region of interest,
obtains input data from brain image data of the subject, and
inputs the input data into the prediction model,
wherein the output unit generates output image data including information on the lesion distribution after recanalization treatment for the subject, by using the prediction model,
wherein the prediction model includes a success prediction model that is learned using pre-treatment and post-treatment brain image data of a plurality of first patients who have modified Treatment In Cerebral Infarction (mTICI) scores of 2b and 3 among the plurality of previous patients, and a failure prediction model that is learned using pre-treatment and post-treatment brain image data of a plurality of second patients who have mTICI scores of 0, 1 and 2a among the plurality of previous patients,
wherein the matched brain image data includes first diffusion weighted image (DWI) data obtained before treatment, perfusion weighted image (PWI) data before treatment, and second diffusion weighted image (DWI) data obtained after treatment, and
wherein the control unit
calculates an apparent diffusion coefficient (ADC) from the first diffusion weighted image (DWI) data,
calculates relative time to peak (rTTP) from the perfusion weighted image (PWI) data before treatment to obtain an rTTP map, and
selects the region of interest from the first diffusion weighted image (DWI) data, the perfusion weighted image (PWI) data before treatment, and the second diffusion weighted image (DWI) data.

6. The device for predicting a brain tissue lesion distribution of claim 5, wherein the control unit
selects a symmetric region corresponding to a normal region from the brain image data, and
extracts the deformation data for each voxel with respect to the symmetric region to obtain the learning input data, and
wherein the symmetric region is selected for the first diffusion weighted image (DWI) data and the perfusion weighted image (PWI) data before treatment.

7. The device for predicting a brain tissue lesion distribution of claim 5, wherein the output unit
generates first output image data including information on the lesion distribution after failure of recanalization treatment for the subject, based on the input data input into the failure prediction model, and generates second output image data including information on the lesion distribution after success of the recanalization treatment for the subject, based on the input data input into the success prediction model.

8. The device for predicting a brain tissue lesion distribution of claim 7, wherein the output unit determines whether or not the recanalization treatment is to be performed for the subject by comparing the first output image data with the second output image data.

9. A non-transitory computer-readable storage medium having stored therein instructions which, when executed by a computer, cause the computer to perform a method of predicting a brain tissue lesion distribution, the method comprising: a model learning operation of learning a prediction model for predicting a brain tissue lesion distribution of a subject by using brain image data of a plurality of previous patients;

an input obtaining operation of obtaining input data from brain image data of the subject;

an input operation of inputting the input data into the prediction model; and an output operation of generating output image data including information on the lesion distribution after recanalization treatment for the subject by using the prediction model, and wherein the prediction model includes a success prediction model that is learned using pre-treatment and post-treatment brain image data of a plurality of first patients who have modified Treatment In Cerebral Infarction (mTICI) scores of 2b and 3 among the plurality of previous patients, and a failure prediction model that is learned using pre-treatment and post-treatment brain image data of a plurality of second patients who have mTICI scores of 0, 1 and 2a among the plurality of previous patients, wherein the brain image data is matched in an image matching operation that includes first diffusion weighted image (DWI) data obtained before treatment, perfusion weighted image (PWI) data before treatment, and second diffusion weighted image (DWI) data obtained after treatment, and wherein a calculating and selecting operation includes an operation of calculating an apparent diffusion coefficient (ADC) from the first diffusion weighted image (DWI) data;

an operation of calculating relative time to peak (rTTP) from the perfusion weighted image (PWI) data before treatment to obtain an rTTP map; and an operation of selecting the region of interest from the first diffusion weighted image (DWI) data, the perfusion weighted image (PWI) data before treatment, and the second diffusion weighted image (DWI) data.

* * * * *